United States Patent [19]

Brown et al.

[11] Patent Number: 4,612,035

[45] Date of Patent: Sep. 16, 1986

[54] HERBICIDAL N-[(4-BROMO-6-METHOXYPYRIMIDIN-2-YL)AMINOCARBONYL]-2,3-DIHYDRO-(2-METHYL)BENZO[b]THIOPHENE-7-SULFONAMIDES, 1,1-DIOXIDE

[75] Inventors: Hugh M. Brown, West Grove, Pa.; Robert J. Pasteris, Wilmington, Del.

[73] Assignee: E. I. Du Pont de Nemours and Company, Wilmington, Del.

[21] Appl. No.: 608,556

[22] Filed: May 9, 1984

[51] Int. Cl.$^4$ .................. A01N 43/02; C07D 239/02
[52] U.S. Cl. ........................................... 71/90; 71/92; 544/320; 544/321
[58] Field of Search ............... 544/320, 331; 71/92, 71/93, 90

[56] References Cited

U.S. PATENT DOCUMENTS

| | | | |
|---|---|---|---|
| 3,637,366 | 1/1972 | Wietelmann et al. | 71/92 |
| 4,127,405 | 11/1978 | Levitt | 544/211 |
| 4,441,910 | 4/1984 | Shapiro | 544/320 |
| 4,465,506 | 8/1984 | Welch | 544/332 |
| 4,484,939 | 11/1984 | Tseng | 544/332 |
| 4,494,979 | 1/1985 | Rorer | 544/332 |
| 4,514,211 | 4/1985 | Rorer | 71/93 |

FOREIGN PATENT DOCUMENTS

| | | |
|---|---|---|
| 1468747 | 1/1967 | France . |
| 121788 | 9/1966 | Netherlands . |
| 835165 | 4/1984 | South Africa . |

OTHER PUBLICATIONS

W. Logemann et al., Chem. Abst. 53:18052g (1959).
Jan Wojciechowski, Chem. Abst. 59:1633e.
Ehrenfreund et al., Chem. Abst. 100-174854e, eq. EP99339, ZA835165.
Comprehensive Organic Chemistry, The Synthesis and Reactions of Organic Compounds, vol. 3, 1979, pp. 345–349, 363–365.

*Primary Examiner*—Donald G. Daus
*Assistant Examiner*—Cecilia Shen

[57] ABSTRACT

Benzofuran and benzothiophene sulfonamides show utility as herbicides and plant growth regulants.

6 Claims, No Drawings

HERBICIDAL N-[(4-BROMO-6-METHOXYPYRIMIDIN-2-YL)AMINOCARBONYL]-2,3-DIHYDRO-(2-METHYL)BENZO[b]THIOPHENE-7-SULFONAMIDES, 1,1-DIOXIDE

BACKGROUND OF THE INVENTION

This invention relates to benzofuran and benzothiophene sulfonamides which are novel. The compounds of this invention and their agriculturally suitable salts, are useful as agricultural chemicals, e.g., plant growth regulants and herbicides.

Netherlands Pat. No. 121,788, published Sept. 15, 1966, discloses the preparation of compounds of the following Formula and their use as general or selective herbicides:

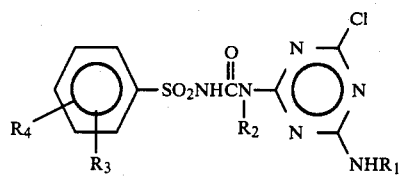

wherein
$R_1$ and $R_2$ may independently be alkyl of 1-4 carbon atoms; and
$R_3$ and $R_4$ may independently be hydrogen, chlorine or alkyl of 1-4 carbon atoms.

U.S. Pat. No. 3,637,366 discloses compounds having the formula:

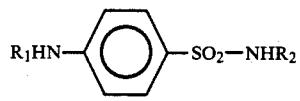

wherein
$R_1$ is hydrogen or lower saturated aliphatic acyl and
$R_2$ is hydrogen, 2-pyrimidinyl, pyridyl, amidino, acetyl or carbamoyl.

The disclosed compounds are said to provide control of crabgrass, cress, endive, clover and *Poa annua*.

French Pat. No. 1,468,747 discloses the following para-substituted phenylsulfonamides as being useful as antidiabetic agents:

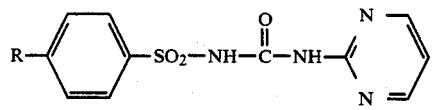

wherein R=H, halogen, $CF_3$ or alkyl.

Logemann et al., Chem. Ab., 53, 18052 g (1959), disclose a number of sulfonamides, including uracil derivatives and those having the formula:

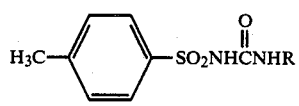

wherein
R is butyl, phenyl or

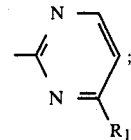

and
$R_1$ is hydrogen or methyl.

When tested for hypoglycemic effect in rats (oral doses of 25 mg/100 g), the compounds in which R is butyl and phenyl were most potent. The others were of low potency or inactive.

Wojciechowski, J. Acta. Polon. Pharm. 19, p. 121-5 (1962) [Chem. Ab., 59 1633 e] describes the synthesis of N-[(2,6-dimethoxypyrimidin-4-yl)aminocarbonyl]-4-methylbenzenesulfonamide:

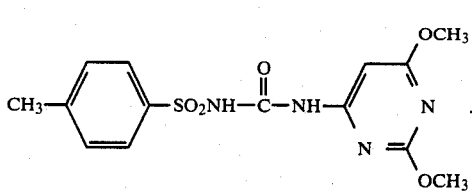

U.S. Pat. No. 4,127,405 teaches compounds which are useful for controlling weeds in wheat having the formula

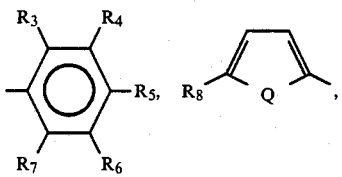

wherein
R is

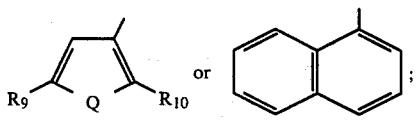

$R_1$ is

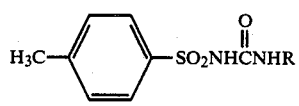

$R_3$ and $R_6$ are independently hydrogen, fluorine, chlorine, bromine, iodine, alkyl of 1-4 carbon atoms, alkoxy of 1-4 carbon atoms, nitro, trifluoromethyl, cyano, $CH_3S(O)_n-$ or $CH_3CH_2S(O)_n$;
$R_4$ is hydrogen, fluorine, chlorine, bromine or methyl;
$R_5$ is hydrogen, fluorine, chlorine, bromine, methyl or methoxy;

$R_7$ is hydrogen, fluorine, chlorine, bromine, alkyl of 1-2 carbon atoms or alkoxy of 1-2 carbon atom;

$R_8$ is hydrogen, methyl, chlorine or bromine;

$R_9$ and $R_{10}$ are independently hydrogen, methyl, chlorine or bromine;

W and Q are independently oxygen or sulfur;

n is 0, 1 or 2;

X is hydrogen, chlorine, bromine, methyl, ethyl, alkoxy of 1-3 carbon atoms, trifluoromethyl, $CH_3S$— or $CH_3OCH_2$—; and Z is methyl or methoxy;

or their agriculturally suitable salts; provided that:

(a) when $R_5$ is other than hydrogen, at least one of $R_3$, $R_4$, $R_6$ and $R_7$ is other than hydrogen and at least two of $R_3$, $R_4$, $R_6$ and $R_7$ must be hydrogen;

(b) when $R_5$ is hydrogen and all of $R_3$, $R_4$, $R_6$ and $R_7$ are other than hydrogen, then all of $R_3$, $R_4$, $R_6$ and $R_7$ must be either chlorine or methyl; and (c) when $R_3$ and $R_7$ are both hydrogen, at least one of $R_4$, $R_5$ or $R_6$ must be hydrogen.

The presence of undesired vegetation causes substantial damage to useful crops, especially agricultural products that satisfy man's basic food and fiber needs, such as cotton, rice, corn, wheat, and the like. The current population explosion and concomitant world food and fiber shortage demand improvements in the efficiency of producing these crops. Prevention or minimizing the loss of a portion of such valuable crops by killing, or inhibiting the growth of undesired vegetation is one way of improving this efficiency. A wide variety of materials useful for killing, or inhibiting (controlling) the growth of undesired vegetation is available; such materials are commonly referred to as herbicides. The need still exists however, for more effective, selective herbicides.

SUMMARY OF THE INVENTION

This invention relates to novel compounds of Formula I, agriculturally suitable compositions containing them and their method-of-use as selective preemergent or postemergent herbicides.

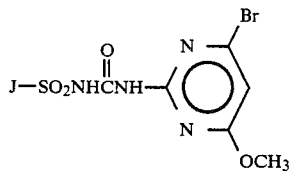

wherein
J is

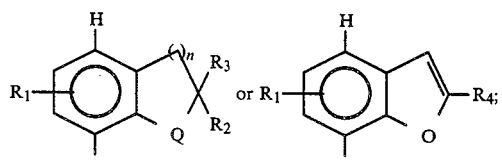

n is 1 or 2;
Q is O, S, SO or $SO_2$;
$R_1$ is H, Cl, $CH_3$ or $OCH_3$;
$R_2$ is H or $C_1$-$C_4$ alkyl;
$R_3$ is H or $CH_3$;
$R_4$ is H or $CH_3$;

provided that when $R_3$ is $CH_3$, then Q is $SO_2$ and $R_2$ is $CH_3$; and their agriculturally suitable salts.

Specifically preferred are:

N-[(4-bromo-6-methoxypyrimidin-2-yl)aminocarbonyl]-2,3-dihydrobenzo[b]thiophene-7-sulfonamide, 1,1-dioxide, m.p. 238°-240° C.; and N-[(4-bromo-6-methoxypyrimidin-2-yl)aminocarbonyl]-2,3-dihydro-2-methylbenzo[b]thiophene-7-sulfonamide, 1,1dioxide, m.p. 225°-227° C.

DETAILED DESCRIPTION OF THE INVENTION

Synthesis

The compounds of Formula I where Q is other than SO can be prepared by reacting the appropriate sulfonyl isocyanate of Formula II with 2-amino-4-bromo-6-methoxypyrimidine III as shown in Equation 1.

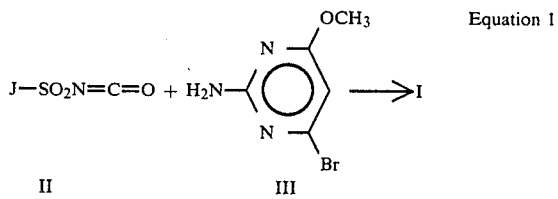

Equation 1

The reaction is carried out at 25° to 100° C. in an inert, aprotic solvent such as methylene chloride or xylene for 0.5 to 24 hours as taught in U.S. Pat. No. 4,127,405.

Alternatively, compounds of Formula I can be prepared by reacting a sulfonyl carbamate of Formula IV with amine III as shown in Equation 2.

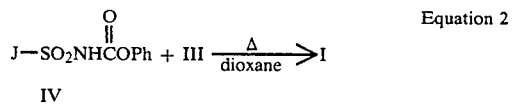

Equation 2

The reaction is carried out at 50° to 100° C. in a solvent such as dioxane for 0.5 to 24 hours as taught in EPO Publication No. 44,807. The required carbamates IV are prepared by reacting the corresponding sulfonamides V with diphenylcarbonate or phenylchloroformate in the presence of base.

The compounds of Formula I can also be prepared by reacting a sulfonamide of Formula V with O-phenyl-N-(4-bromo-6-methoxypyrimidin-2-yl)carbamate VI in the presence of base as shown in Equation 3.

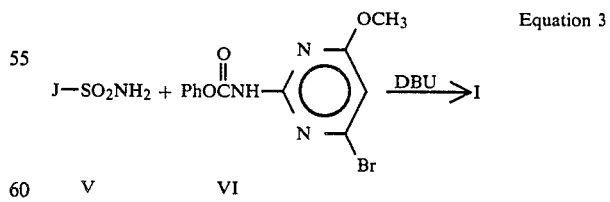

Equation 3

The reaction is carried out at 0° to 50° C. in an inert solvent such as acetonitrile for 0.1 to 24 hours in the presence of a base such as 1,8-diazabicyclo[5.4.0]undec-7-ene (DBU) as taught in EPO Publication No. 44,807. The required carbamate VI is prepared by reacting amine III with diphenylcarbonate or phenylchloroformate in the presence of base.

Compounds of Formula I where Q is SO can be prepared via oxidation of the corresponding compounds of Formula I where Q is S by standard methods known to one skilled in the art.

The intermediate sulfonyl isocyanates of Formula II and sulfonamides of Formula V can be prepared by methods which would be obvious to one skilled in the art such as those taught in EPO Publication No. 79,683 and in South African Patent Application No. 83/5165.

2-Amino-4-bromo-6-methoxypyrimidine III is known, see T. Hirayama, et. al. *Heterocycles*, 2, 461 (1974) and *Chem. Pharm. Bull.* 24, 507 (1976). It can also be prepared by contacting 2-amino-4,6-dibromopyrimidine with one equivalent of sodium methoxide in methanol.

Agriculturally suitable salts of compounds of Formula I are also useful herbicides and can be prepared in a number of ways known to the art. For example, metal salts can be made by contacting compounds of Formula I with a solution of an alkali or alkaline earth metal salt having a sufficiently basic anion (e.g., hydroxide, alkoxide, carbonate or hydroxide). Quaternary amine salts can be made by similar techniques.

Salts of compounds of Formula I can also be prepared by exchange of one cation for another. Cationic exchange can be effected by direct contact of an aqueous solution of a salt of a compound of Formula I (e.g., alkali or quaternary amine salt) with a solution containing the cation to be exchanged. This method is most effective when the desired salt containing the exchanged cation is insoluble in water and can be separated by filtration.

Exchange may also be effected by passing an aqueous solution of a salt of a compound of Formula I (e.g., an alkali metal or quaternary amine salt) through a column packed with a cation exchange resin containing the cation to be exchanged for that of the original salt and the desired product is eluted from the column. This method is particularly useful when the desired salt is water-soluble.

Acid addition salts, useful in this invention, can be obtained by reacting a compound of Formula I with a suitable acid, e.g., p-toluenesulfonic acid, trichloroacetic acid or the like.

The following example teaches the synthesis of a compound of this invention in greater detail.

EXAMPLE 1

N-[(4-Bromo-6-methoxypyrimidin-2-yl)aminocarbonyl]-2,3-dihydrobenzo[b]thiophene-7-sulfonamide, 1,1-dioxide A suspension of 5.0 g (20 mmol) of 2,3-dihydrobenzo[b]thiophene-7-sulfonamide-1,1-dioxide in 50 mL of thionyl chloride was refluxed for 40 hours, cooled, diluted with 100 mL of dry toluene and fractionally distilled to remove excess thionyl chloride. The cooled toluene solution was contacted with 2 drops of pyridine and 3 mL of liquified phosgene and the mixture was refluxed for 3 hours, cooled and concentrated in vacuo to give 5.8 g of 2,3-dihydrobenzo[b]thiophene-7-sulfonylisocyanate-1,1-dioxide as a brown powder whose IR spectrum exhibited a strong band at 2250 cm$^{-1}$.

A solution of 1.4 g (5 mmol) of the crude isocyanate and 0.82 g (4 mmol) of 2-amino-4-bromo-6-methoxypyrimidine in 20 mL of dry methylene chloride was heated to reflux for 5 minutes and stirred at room temperature for 16 hours. The resulting precipitate was filtered, washed with dry methylene chloride and anhydrous ether and air dried to give 1.6 g of the title compound as a white powder, m.p. 238°–240° C.

200 MHz $^1$H NMR (DMSO-d$_6$): δ 12.2 (br, 1H, NH); 10.9 (b, 1H, NH); 8.1 (m, 1H, arom); 7.9 (m, 2H, arom); 7.0 (s, 1H, CH) 4.0 (s, 3H, OCH$_3$); 3.7 (m, 2H, CH$_2$); and 3.4 (m, 2H, CH$_2$) ppm.

IR (nujol): 3380, 1730, 1710 cm$^{-1}$.

The following compounds can be prepared by one skilled in the art using the proper reactants and the procedures outlined above.

TABLE I

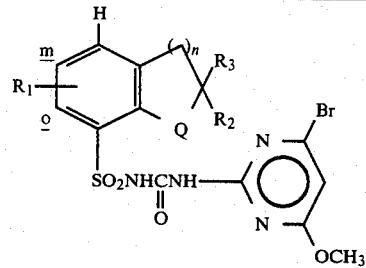

| n | Q | R$_1$ | R$_2$ | R$_3$ | m.p. (°C.) |
|---|---|---|---|---|---|
| 1 | O | H | H | H | 197–201 |
| 1 | O | H | CH$_3$ | H | |
| 1 | O | H | CH$_2$CH$_3$ | H | |
| 1 | O | H | CH$_2$CH$_2$CH$_3$ | H | |
| 1 | O | H | CH$_2$CH$_2$CH$_2$CH$_3$ | H | |
| 1 | O | H | CH(CH$_3$)$_2$ | H | |
| 1 | O | H | CH(CH$_3$)CH$_2$CH$_3$ | H | |
| 1 | O | H | CH$_2$CH(CH$_3$)$_2$ | H | |
| 1 | O | o-Cl | H | H | |
| 1 | O | o-Cl | CH$_3$ | H | |
| 1 | O | o-Cl | CH$_2$CH$_3$ | H | |
| 1 | O | o-Cl | CH$_2$CH$_2$CH$_3$ | H | |
| 1 | O | o-Cl | CH$_2$CH$_2$CH$_2$CH$_3$ | H | |
| 1 | O | o-Cl | CH(CH$_3$)$_2$ | H | |
| 1 | O | o-Cl | CH(CH$_3$)CH$_2$CH$_3$ | H | |
| 1 | O | o-Cl | CH$_2$CH(CH$_3$)$_2$ | H | |
| 1 | O | m-Cl | H | H | |
| 1 | O | m-Cl | CH$_3$ | H | 208–211 |
| 1 | O | m-Cl | CH$_2$CH$_3$ | H | |
| 1 | O | m-Cl | CH$_2$CH$_2$CH$_3$ | H | |
| 1 | O | m-Cl | CH$_2$CH$_2$CH$_2$CH$_3$ | H | |
| 1 | O | m-Cl | CH(CH$_3$)$_2$ | H | |
| 1 | O | m-Cl | CH(CH$_3$)CH$_2$CH$_3$ | H | |
| 1 | O | m-Cl | CH$_2$CH(CH$_3$)$_2$ | H | |
| 1 | O | o-CH$_3$ | H | H | |
| 1 | O | o-CH$_3$ | CH$_3$ | H | |
| 1 | O | o-CH$_3$ | CH$_2$CH$_3$ | H | |
| 1 | O | o-CH$_3$ | CH$_2$CH$_2$CH$_3$ | H | |
| 1 | O | o-CH$_3$ | CH$_2$CH$_2$CH$_2$CH$_3$ | H | |
| 1 | O | o-CH$_3$ | CH(CH$_3$)$_2$ | H | |
| 1 | O | o-CH$_3$ | CH(CH$_3$)CH$_2$CH$_3$ | H | |
| 1 | O | o-CH$_3$ | CH$_2$CH(CH$_3$)$_2$ | H | |
| 1 | O | m-CH$_3$ | H | H | |
| 1 | O | m-CH$_3$ | CH$_3$ | H | |
| 1 | O | m-CH$_3$ | CH$_2$CH$_3$ | H | |
| 1 | O | m-CH$_3$ | CH$_2$CH$_2$CH$_3$ | H | |
| 1 | O | m-CH$_3$ | CH$_2$CH$_2$CH$_2$CH$_3$ | H | |
| 1 | O | m-CH$_3$ | CH(CH$_3$)$_2$ | H | |
| 1 | O | m-CH$_3$ | CH(CH$_3$)CH$_2$CH$_3$ | H | |
| 1 | O | m-CH$_3$ | CH$_2$CH(CH$_3$)$_2$ | H | |
| 1 | O | o-OCH$_3$ | H | H | |
| 1 | O | o-OCH$_3$ | CH$_3$ | H | |
| 1 | O | o-OCH$_3$ | CH$_2$CH$_3$ | H | |
| 1 | O | o-OCH$_3$ | CH$_2$CH$_2$CH$_3$ | H | |
| 1 | O | o-OCH$_3$ | CH$_2$CH$_2$CH$_2$CH$_3$ | H | |
| 1 | O | o-OCH$_3$ | CH(CH$_3$)$_2$ | H | |
| 1 | O | o-OCH$_3$ | CH(CH$_3$)CH$_2$CH$_3$ | H | |
| 1 | O | o-OCH$_3$ | CH$_2$CH(CH$_3$)$_2$ | H | |
| 1 | O | m-OCH$_3$ | H | H | |
| 1 | O | m-OCH$_3$ | CH$_3$ | H | |
| 1 | O | m-OCH$_3$ | CH$_2$CH$_3$ | H | |
| 1 | O | m-OCH$_3$ | CH$_2$CH$_2$CH$_3$ | H | |
| 1 | O | m-OCH$_3$ | CH$_2$CH$_2$CH$_2$CH$_3$ | H | |
| 1 | O | m-OCH$_3$ | CH(CH$_3$)$_2$ | H | |

TABLE I-continued

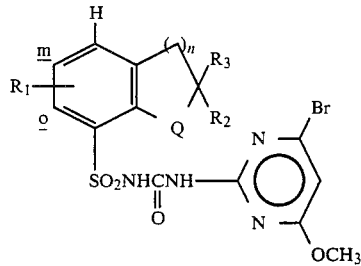

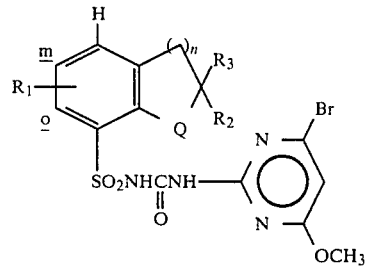

| n | Q | R₁ | R₂ | R₃ | m.p. (°C.) |
|---|---|---|---|---|---|
| 1 | O | m-OCH₃ | CH(CH₃)CH₂CH₃ | H | |
| 1 | O | m-OCH₃ | CH₂CH(CH₃)₂ | H | |
| 1 | S | H | H | H | |
| 1 | S | H | CH₃ | H | |
| 1 | S | H | CH₂CH₃ | H | |
| 1 | S | H | CH₂CH₂CH₃ | H | |
| 1 | S | H | CH₂CH₂CH₂CH₃ | H | |
| 1 | S | H | CH(CH₃)₂ | H | |
| 1 | S | H | CH(CH₃)CH₂CH₃ | H | |
| 1 | S | H | CH₂CH(CH₃)₂ | H | |
| 1 | S | o-Cl | H | H | |
| 1 | S | o-Cl | CH₃ | H | |
| 1 | S | o-Cl | CH₂CH₃ | H | |
| 1 | S | o-Cl | CH₂CH₂CH₃ | H | |
| 1 | S | o-Cl | CH₂CH₂CH₂CH₃ | H | |
| 1 | S | o-Cl | CH(CH₃)₂ | H | |
| 1 | S | o-Cl | CH(CH₃)CH₂CH₃ | H | |
| 1 | S | o-Cl | CH₂CH(CH₃)₂ | H | |
| 1 | S | m-Cl | H | H | |
| 1 | S | m-Cl | CH₃ | H | |
| 1 | S | m-Cl | CH₂CH₃ | H | |
| 1 | S | m-Cl | CH₂CH₂CH₃ | H | |
| 1 | S | m-Cl | CH₂CH₂CH₂CH₃ | H | |
| 1 | S | m-Cl | CH(CH₃)₂ | H | |
| 1 | S | m-Cl | CH(CH₃)CH₂CH₃ | H | |
| 1 | S | m-Cl | CH₂CH(CH₃)₂ | H | |
| 1 | S | o-CH₃ | H | H | |
| 1 | S | o-CH₃ | CH₃ | H | |
| 1 | S | o-CH₃ | CH₂CH₃ | H | |
| 1 | S | o-CH₃ | CH₂CH₂CH₃ | H | |
| 1 | S | o-CH₃ | CH₂CH₂CH₂CH₃ | H | |
| 1 | S | o-CH₃ | CH(CH₃)₂ | H | |
| 1 | S | o-CH₃ | CH(CH₃)CH₂CH₃ | H | |
| 1 | S | o-CH₃ | CH₂CH(CH₃)₂ | H | |
| 1 | S | m-CH₃ | H | H | |
| 1 | S | m-CH₃ | CH₃ | H | |
| 1 | S | m-CH₃ | CH₂CH₃ | H | |
| 1 | S | m-CH₃ | CH₂CH₂CH₃ | H | |
| 1 | S | m-CH₃ | CH₂CH₂CH₂CH₃ | H | |
| 1 | S | m-CH₃ | CH(CH₃)₂ | H | |
| 1 | S | m-CH₃ | CH(CH₃)CH₂CH₃ | H | |
| 1 | S | m-CH₃ | CH₂CH(CH₃)₂ | H | |
| 1 | S | o-OCH₃ | H | H | |
| 1 | S | o-OCH₃ | CH₃ | H | |
| 1 | S | o-OCH₃ | CH₂CH₃ | H | |
| 1 | S | o-OCH₃ | CH₂CH₂CH₃ | H | |
| 1 | S | o-OCH₃ | CH₂CH₂CH₂CH₃ | H | |
| 1 | S | o-OCH₃ | CH(CH₃)₂ | H | |
| 1 | S | o-OCH₃ | CH(CH₃)CH₂CH₃ | H | |
| 1 | S | o-OCH₃ | CH₂CH(CH₃)₂ | H | |
| 1 | S | m-OCH₃ | H | H | |
| 1 | S | m-OCH₃ | CH₃ | H | |
| 1 | S | m-OCH₃ | CH₂CH₃ | H | |
| 1 | S | m-OCH₃ | CH₂CH₂CH₃ | H | |
| 1 | S | m-OCH₃ | CH₂CH₂CH₂CH₃ | H | |
| 1 | S | m-OCH₃ | CH(CH₃)₂ | H | |
| 1 | S | m-OCH₃ | CH(CH₃)CH₂CH₃ | H | |
| 1 | S | m-OCH₃ | CH₂CH(CH₃)₂ | H | |
| 1 | SO | H | H | H | |
| 1 | SO | H | CH₃ | H | |
| 1 | SO | H | CH₂CH₃ | H | |
| 1 | SO | H | CH₂CH₂CH₃ | H | |
| 1 | SO | H | CH₂CH₂CH₂CH₃ | H | |
| 1 | SO | H | CH(CH₃)₂ | H | |
| 1 | SO | H | CH(CH₃)CH₂CH₃ | H | |
| 1 | SO | H | CH₂CH(CH₃)₂ | H | |
| 1 | SO | o-Cl | H | H | |
| 1 | SO | o-Cl | CH₃ | H | |
| 1 | SO | o-Cl | CH₂CH₃ | H | |
| 1 | SO | o-Cl | CH₂CH₂CH₃ | H | |
| 1 | SO | o-Cl | CH₂CH₂CH₂CH₃ | H | |
| 1 | SO | o-Cl | CH(CH₃)₂ | H | |
| 1 | SO | o-Cl | CH(CH₃)CH₂CH₃ | H | |
| 1 | SO | o-Cl | CH₂CH(CH₃)₂ | H | |
| 1 | SO | m-Cl | H | H | |
| 1 | SO | m-Cl | CH₃ | H | |
| 1 | SO | m-Cl | CH₂CH₃ | H | |
| 1 | SO | m-Cl | CH₂CH₂CH₃ | H | |
| 1 | SO | m-Cl | CH₂CH₂CH₂CH₃ | H | |
| 1 | SO | m-Cl | CH(CH₃)₂ | H | |
| 1 | SO | m-Cl | CH(CH₃)CH₂CH₃ | H | |
| 1 | SO | m-Cl | CH₂CH(CH₃)₂ | H | |
| 1 | SO | o-CH₃ | H | H | |
| 1 | SO | o-CH₃ | CH₃ | H | |
| 1 | SO | o-CH₃ | CH₂CH₃ | H | |
| 1 | SO | o-CH₃ | CH₂CH₂CH₃ | H | |
| 1 | SO | o-CH₃ | CH₂CH₂CH₂CH₃ | H | |
| 1 | SO | o-CH₃ | CH(CH₃)₂ | H | |
| 1 | SO | o-CH₃ | CH(CH₃)CH₂CH₃ | H | |
| 1 | SO | o-CH₃ | CH₂CH(CH₃)₂ | H | |
| 1 | SO | m-CH₃ | H | H | |
| 1 | SO | m-CH₃ | CH₃ | H | |
| 1 | SO | m-CH₃ | CH₂CH₃ | H | |
| 1 | SO | m-CH₃ | CH₂CH₂CH₃ | H | |
| 1 | SO | m-CH₃ | CH₂CH₂CH₂CH₃ | H | |
| 1 | SO | m-CH₃ | CH(CH₃)₂ | H | |
| 1 | SO | m-CH₃ | CH(CH₃)CH₂CH₃ | H | |
| 1 | SO | m-CH₃ | CH₂CH(CH₃)₂ | H | |
| 1 | SO | o-OCH₃ | H | H | |
| 1 | SO | o-OCH₃ | CH₃ | H | |
| 1 | SO | o-OCH₃ | CH₂CH₃ | H | |
| 1 | SO | o-OCH₃ | CH₂CH₂CH₃ | H | |
| 1 | SO | o-OCH₃ | CH₂CH₂CH₂CH₃ | H | |
| 1 | SO | o-OCH₃ | CH(CH₃)₂ | H | |
| 1 | SO | o-OCH₃ | CH(CH₃)CH₂CH₃ | H | |
| 1 | SO | o-OCH₃ | CH₂CH(CH₃)₂ | H | |
| 1 | SO | m-OCH₃ | H | H | |
| 1 | SO | m-OCH₃ | CH₃ | H | |
| 1 | SO | m-OCH₃ | CH₂CH₃ | H | |
| 1 | SO | m-OCH₃ | CH₂CH₂CH₃ | H | |
| 1 | SO | m-OCH₃ | CH₂CH₂CH₂CH₃ | H | |
| 1 | SO | m-OCH₃ | CH(CH₃)₂ | H | |
| 1 | SO | m-OCH₃ | CH(CH₃)CH₂CH₃ | H | |
| 1 | SO | m-OCH₃ | CH₂CH(CH₃)₂ | H | |
| 1 | SO₂ | H | H | H | 238–240 |
| 1 | SO₂ | H | CH₃ | H | 225–227 |
| 1 | SO₂ | H | CH₃ | CH₃ | 235–237 |
| 1 | SO₂ | H | CH₂CH₃ | H | |
| 1 | SO₂ | H | CH₂CH₂CH₃ | H | |
| 1 | SO₂ | H | CH₂CH₂CH₂CH₃ | H | |
| 1 | SO₂ | H | CH(CH₃)₂ | H | |
| 1 | SO₂ | H | CH(CH₃)CH₂CH₃ | H | |
| 1 | SO₂ | H | CH₂CH(CH₃)₂ | H | |
| 1 | SO₂ | o-Cl | H | H | |
| 1 | SO₂ | o-Cl | CH₃ | H | |
| 1 | SO₂ | o-Cl | CH₃ | CH₃ | |
| 1 | SO₂ | o-Cl | CH₂CH₃ | H | |
| 1 | SO₂ | o-Cl | CH₂CH₂CH₃ | H | |
| 1 | SO₂ | o-Cl | CH₂CH₂CH₂CH₃ | H | |
| 1 | SO₂ | o-Cl | CH(CH₃)₂ | H | |
| 1 | SO₂ | o-Cl | CH(CH₃)CH₂CH₃ | H | |
| 1 | SO₂ | o-Cl | CH₂CH(CH₃)₂ | H | |
| 1 | SO₂ | m-Cl | H | H | |
| 1 | SO₂ | m-Cl | CH₃ | H | |

TABLE I-continued

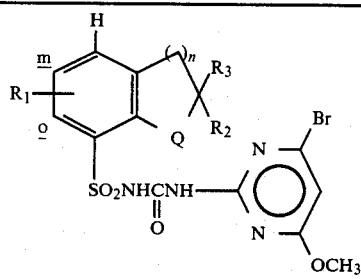

| n | Q | R1 | R2 | R3 | m.p. (°C.) |
|---|---|---|---|---|---|
| 1 | SO2 | m-Cl | CH3 | CH3 | |
| 1 | SO2 | m-Cl | CH2CH3 | H | |
| 1 | SO2 | m-Cl | CH2CH2CH3 | H | |
| 1 | SO2 | m-Cl | CH2CH2CH2CH3 | H | |
| 1 | SO2 | m-Cl | CH(CH3)2 | H | |
| 1 | SO2 | m-Cl | CH(CH3)CH2CH3 | H | |
| 1 | SO2 | m-Cl | CH2CH(CH3)2 | H | |
| 1 | SO2 | o-CH3 | H | H | |
| 1 | SO2 | o-CH3 | CH3 | H | |
| 1 | SO2 | o-CH3 | CH3 | CH3 | |
| 1 | SO2 | o-CH3 | CH2CH3 | H | |
| 1 | SO2 | o-CH3 | CH2CH2CH3 | H | |
| 1 | SO2 | o-CH3 | CH2CH2CH2CH3 | H | |
| 1 | SO2 | o-CH3 | CH(CH3)2 | H | |
| 1 | SO2 | o-CH3 | CH(CH3)CH2CH3 | H | |
| 1 | SO2 | o-CH3 | CH2CH(CH3)2 | H | |
| 1 | SO2 | m-CH3 | H | H | |
| 1 | SO2 | m-CH3 | CH3 | H | |
| 1 | SO2 | m-CH3 | CH3 | CH3 | |
| 1 | SO2 | m-CH3 | CH2CH3 | H | |
| 1 | SO2 | m-CH3 | CH2CH2CH3 | H | |
| 1 | SO2 | m-CH3 | CH2CH2CH2CH3 | H | |
| 1 | SO2 | m-CH3 | CH(CH3)2 | H | |
| 1 | SO2 | m-CH3 | CH(CH3)CH2CH3 | H | |
| 1 | SO2 | m-CH3 | CH2CH(CH3)2 | H | |
| 1 | SO2 | o-OCH3 | H | H | |
| 1 | SO2 | o-OCH3 | CH3 | H | |
| 1 | SO2 | o-OCH3 | CH3 | CH3 | |
| 1 | SO2 | o-OCH3 | CH2CH3 | H | |
| 1 | SO2 | o-OCH3 | CH2CH2CH3 | H | |
| 1 | SO2 | o-OCH3 | CH2CH2CH2CH3 | H | |
| 1 | SO2 | o-OCH3 | CH(CH3)2 | H | |
| 1 | SO2 | o-OCH3 | CH(CH3)CH2CH3 | H | |
| 1 | SO2 | o-OCH3 | CH2CH(CH3)2 | H | |
| 1 | SO2 | m-OCH3 | H | H | |
| 1 | SO2 | m-OCH3 | CH3 | H | |
| 1 | SO2 | m-OCH3 | CH3 | CH3 | |
| 1 | SO2 | m-OCH3 | CH2CH3 | H | |
| 1 | SO2 | m-OCH3 | CH2CH2CH3 | H | |
| 1 | SO2 | m-OCH3 | CH2CH2CH2CH3 | H | |
| 1 | SO2 | m-OCH3 | CH(CH3)2 | H | |
| 1 | SO2 | m-OCH3 | CH(CH3)CH2CH3 | H | |
| 1 | SO2 | m-OCH3 | CH2CH(CH3)2 | H | |
| 2 | O | H | H | H | |
| 2 | O | H | CH3 | H | |
| 2 | O | H | CH2CH3 | H | |
| 2 | O | H | CH2CH2CH3 | H | |
| 2 | O | H | CH2CH2CH2CH3 | H | |
| 2 | O | H | CH(CH3)2 | H | |
| 2 | O | H | CH(CH3)CH2CH3 | H | |
| 2 | O | H | CH2CH(CH3)2 | H | |
| 2 | O | o-Cl | H | H | |
| 2 | O | o-Cl | CH3 | H | |
| 2 | O | o-Cl | CH2CH3 | H | |
| 2 | O | o-Cl | CH2CH2CH3 | H | |
| 2 | O | o-Cl | CH2CH2CH2CH3 | H | |
| 2 | O | o-Cl | CH(CH3)2 | H | |
| 2 | O | o-Cl | CH(CH3)CH2CH3 | H | |
| 2 | O | o-Cl | CH2CH(CH3)2 | H | |
| 2 | O | m-Cl | H | H | |
| 2 | O | m-Cl | CH3 | H | |
| 2 | O | m-Cl | CH2CH3 | H | |
| 2 | O | m-Cl | CH2CH2CH3 | H | |
| 2 | O | m-Cl | CH2CH2CH2CH3 | H | |
| 2 | O | m-Cl | CH(CH3)2 | H | |
| 2 | O | m-Cl | CH(CH3)CH2CH3 | H | |
| 2 | O | m-Cl | CH2CH(CH3)2 | H | |
| 2 | O | o-CH3 | H | H | |
| 2 | O | o-CH3 | CH3 | H | |
| 2 | O | o-CH3 | CH2CH3 | H | |
| 2 | O | o-CH3 | CH2CH2CH3 | H | |
| 2 | O | o-CH3 | CH2CH2CH2CH3 | H | |
| 2 | O | o-CH3 | CH(CH3)2 | H | |
| 2 | O | o-CH3 | CH(CH3)CH2CH3 | H | |
| 2 | O | o-CH3 | CH2CH(CH3)2 | H | |
| 2 | O | m-CH3 | H | H | |
| 2 | O | m-CH3 | CH3 | H | |
| 2 | O | m-CH3 | CH2CH3 | H | |
| 2 | O | m-CH3 | CH2CH2CH3 | H | |
| 2 | O | m-CH3 | CH2CH2CH2CH3 | H | |
| 2 | O | m-CH3 | CH(CH3)2 | H | |
| 2 | O | m-CH3 | CH(CH3)CH2CH3 | H | |
| 2 | O | m-CH3 | CH2CH(CH3)2 | H | |
| 2 | O | o-OCH3 | H | H | |
| 2 | O | o-OCH3 | CH3 | H | |
| 2 | O | o-OCH3 | CH2CH3 | H | |
| 2 | O | o-OCH3 | CH2CH2CH3 | H | |
| 2 | O | o-OCH3 | CH2CH2CH2CH3 | H | |
| 2 | O | o-OCH3 | CH(CH3)2 | H | |
| 2 | O | o-OCH3 | CH(CH3)CH2CH3 | H | |
| 2 | O | o-OCH3 | CH2CH(CH3)2 | H | |
| 2 | O | m-OCH3 | H | H | |
| 2 | O | m-OCH3 | CH3 | H | |
| 2 | O | m-OCH3 | CH2CH3 | H | |
| 2 | O | m-OCH3 | CH2CH2CH3 | H | |
| 2 | O | m-OCH3 | CH2CH2CH2CH3 | H | |
| 2 | O | m-OCH3 | CH(CH3)2 | H | |
| 2 | O | m-OCH3 | CH(CH3)CH2CH3 | H | |
| 2 | O | m-OCH3 | CH2CH(CH3)2 | H | |
| 2 | S | H | H | H | |
| 2 | S | H | CH3 | H | |
| 2 | S | H | CH2CH3 | H | |
| 2 | S | H | CH2CH2CH3 | H | |
| 2 | S | H | CH2CH2CH2CH3 | H | |
| 2 | S | H | CH(CH3)2 | H | |
| 2 | S | H | CH(CH3)CH2CH3 | H | |
| 2 | S | H | CH2CH(CH3)2 | H | |
| 2 | S | o-Cl | H | H | |
| 2 | S | o-Cl | CH3 | H | |
| 2 | S | o-Cl | CH2CH3 | H | |
| 2 | S | o-Cl | CH2CH2CH3 | H | |
| 2 | S | o-Cl | CH2CH2CH2CH3 | H | |
| 2 | S | o-Cl | CH(CH3)2 | H | |
| 2 | S | o-Cl | CH(CH3)CH2CH3 | H | |
| 2 | S | o-Cl | CH2CH(CH3)2 | H | |
| 2 | S | m-Cl | H | H | |
| 2 | S | m-Cl | CH3 | H | |
| 2 | S | m-Cl | CH2CH3 | H | |
| 2 | S | m-Cl | CH2CH2CH3 | H | |
| 2 | S | m-Cl | CH2CH2CH2CH3 | H | |
| 2 | S | m-Cl | CH(CH3)2 | H | |
| 2 | S | m-Cl | CH(CH3)CH2CH3 | H | |
| 2 | S | m-Cl | CH2CH(CH3)2 | H | |
| 2 | S | o-CH3 | H | H | |
| 2 | S | o-CH3 | CH3 | H | |
| 2 | S | o-CH3 | CH2CH3 | H | |
| 2 | S | o-CH3 | CH2CH2CH3 | H | |
| 2 | S | o-CH3 | CH2CH2CH2CH3 | H | |
| 2 | S | o-CH3 | CH(CH3)2 | H | |
| 2 | S | o-CH3 | CH(CH3)CH2CH3 | H | |
| 2 | S | o-CH3 | CH2CH(CH3)2 | H | |
| 2 | S | m-CH3 | H | H | |
| 2 | S | m-CH3 | CH3 | H | |
| 2 | S | m-CH3 | CH2CH3 | H | |

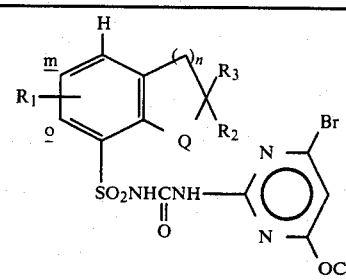

TABLE I-continued

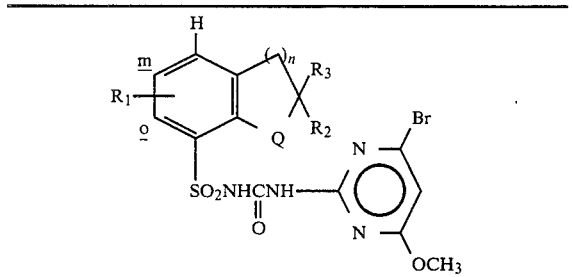

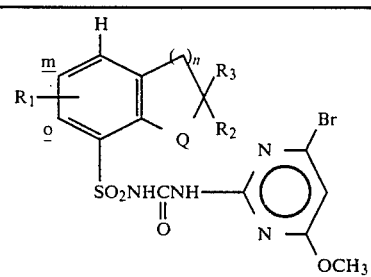

| n | Q | R₁ | R₂ | R₃ | m.p. (°C.) |
|---|---|---|---|---|---|
| 2 | S | m-CH₃ | CH₂CH₂CH₃ | H | |
| 2 | S | m-CH₃ | CH₂CH₂CH₂CH₃ | H | |
| 2 | S | m-CH₃ | CH(CH₃)₂ | H | |
| 2 | S | m-CH₃ | CH(CH₃)CH₂CH₃ | H | |
| 2 | S | m-CH₃ | CH₂CH(CH₃)₂ | H | |
| 2 | S | o-OCH₃ | H | H | |
| 2 | S | o-OCH₃ | CH₃ | H | |
| 2 | S | o-OCH₃ | CH₂CH₃ | H | |
| 2 | S | o-OCH₃ | CH₂CH₂CH₃ | H | |
| 2 | S | o-OCH₃ | CH₂CH₂CH₂CH₃ | H | |
| 2 | S | o-OCH₃ | CH(CH₃)₂ | H | |
| 2 | S | o-OCH₃ | CH(CH₃)CH₂CH₃ | H | |
| 2 | S | o-OCH₃ | CH₂CH(CH₃)₂ | H | |
| 2 | S | m-OCH₃ | H | H | |
| 2 | S | m-OCH₃ | CH₃ | H | |
| 2 | S | m-OCH₃ | CH₂CH₃ | H | |
| 2 | S | m-OCH₃ | CH₂CH₂CH₃ | H | |
| 2 | S | m-OCH₃ | CH₂CH₂CH₂CH₃ | H | |
| 2 | S | m-OCH₃ | CH(CH₃)₂ | H | |
| 2 | S | m-OCH₃ | CH(CH₃)CH₂CH₃ | H | |
| 2 | S | m-OCH₃ | CH₂CH(CH₃)₂ | H | |
| 2 | SO | H | H | H | |
| 2 | SO | H | CH₃ | H | |
| 2 | SO | H | CH₂CH₃ | H | |
| 2 | SO | H | CH₂CH₂CH₃ | H | |
| 2 | SO | H | CH₂CH₂CH₂CH₃ | H | |
| 2 | SO | H | CH(CH₃)₂ | H | |
| 2 | SO | H | CH(CH₃)CH₂CH₃ | H | |
| 2 | SO | H | CH₂CH(CH₃)₂ | H | |
| 2 | SO | o-Cl | H | H | |
| 2 | SO | o-Cl | CH₃ | H | |
| 2 | SO | o-Cl | CH₂CH₃ | H | |
| 2 | SO | o-Cl | CH₂CH₂CH₃ | H | |
| 2 | SO | o-Cl | CH₂CH₂CH₂CH₃ | H | |
| 2 | SO | o-Cl | CH(CH₃)₂ | H | |
| 2 | SO | o-Cl | CH(CH₃)CH₂CH₃ | H | |
| 2 | SO | o-Cl | CH₂CH(CH₃)₂ | H | |
| 2 | SO | m-Cl | H | H | |
| 2 | SO | m-Cl | CH₃ | H | |
| 2 | SO | m-Cl | CH₂CH₃ | H | |
| 2 | SO | m-Cl | CH₂CH₂CH₃ | H | |
| 2 | SO | m-Cl | CH₂CH₂CH₂CH₃ | H | |
| 2 | SO | m-Cl | CH(CH₃)₂ | H | |
| 2 | SO | m-Cl | CH(CH₃)CH₂CH₃ | H | |
| 2 | SO | m-Cl | CH₂CH(CH₃)₂ | H | |
| 2 | SO | o-CH₃ | H | H | |
| 2 | SO | o-CH₃ | CH₃ | H | |
| 2 | SO | o-CH₃ | CH₂CH₃ | H | |
| 2 | SO | o-CH₃ | CH₂CH₂CH₃ | H | |
| 2 | SO | o-CH₃ | CH₂CH₂CH₂CH₃ | H | |
| 2 | SO | o-CH₃ | CH(CH₃)₂ | H | |
| 2 | SO | o-CH₃ | CH(CH₃)CH₂CH₃ | H | |
| 2 | SO | o-CH₃ | CH₂CH(CH₃)₂ | H | |
| 2 | SO | m-CH₃ | H | H | |
| 2 | SO | m-CH₃ | CH₃ | H | |
| 2 | SO | m-CH₃ | CH₂CH₃ | H | |
| 2 | SO | m-CH₃ | CH₂CH₂CH₃ | H | |
| 2 | SO | m-CH₃ | CH₂CH₂CH₂CH₃ | H | |
| 2 | SO | m-CH₃ | CH(CH₃)₂ | H | |
| 2 | SO | m-CH₃ | CH(CH₃)CH₂CH₃ | H | |
| 2 | SO | m-CH₃ | CH₂CH(CH₃)₂ | H | |
| 2 | SO | o-OCH₃ | H | H | |
| 2 | SO | o-OCH₃ | CH₃ | H | |
| 2 | SO | o-OCH₃ | CH₂CH₃ | H | |
| 2 | SO | o-OCH₃ | CH₂CH₂CH₃ | H | |
| 2 | SO | o-OCH₃ | CH₂CH₂CH₂CH₃ | H | |
| 2 | SO | o-OCH₃ | CH(CH₃)₂ | H | |
| 2 | SO | o-OCH₃ | CH(CH₃)CH₂CH₃ | H | |
| 2 | SO | o-OCH₃ | CH₂CH(CH₃)₂ | H | |
| 2 | SO | m-OCH₃ | H | H | |
| 2 | SO | m-OCH₃ | CH₃ | H | |
| 2 | SO | m-OCH₃ | CH₂CH₃ | H | |
| 2 | SO | m-OCH₃ | CH₂CH₂CH₃ | H | |
| 2 | SO | m-OCH₃ | CH₂CH₂CH₂CH₃ | H | |
| 2 | SO | m-OCH₃ | CH(CH₃)₂ | H | |
| 2 | SO | m-OCH₃ | CH(CH₃)CH₂CH₃ | H | |
| 2 | SO | m-OCH₃ | CH₂CH(CH₃)₂ | H | |
| 2 | SO₂ | H | H | H | |
| 2 | SO₂ | H | CH₃ | CH₃ | |
| 2 | SO₂ | H | CH₂CH₃ | H | |
| 2 | SO₂ | H | CH₂CH₂CH₃ | H | |
| 2 | SO₂ | H | CH₂CH₂CH₂CH₃ | H | |
| 2 | SO₂ | H | CH(CH₃)₂ | H | |
| 2 | SO₂ | H | CH(CH₃)CH₂CH₃ | H | |
| 2 | SO₂ | H | CH₂CH(CH₃)₂ | H | |
| 2 | SO₂ | o-Cl | H | H | |
| 2 | SO₂ | o-Cl | CH₃ | H | |
| 2 | SO₂ | o-Cl | CH₃ | CH₃ | |
| 2 | SO₂ | o-Cl | CH₂CH₃ | H | |
| 2 | SO₂ | o-Cl | CH₂CH₂CH₃ | H | |
| 2 | SO₂ | o-Cl | CH₂CH₂CH₂CH₃ | H | |
| 2 | SO₂ | o-Cl | CH(CH₃)₂ | H | |
| 2 | SO₂ | o-Cl | CH(CH₃)CH₂CH₃ | H | |
| 2 | SO₂ | o-Cl | CH₂CH(CH₃)₂ | H | |
| 2 | SO₂ | m-Cl | H | H | |
| 2 | SO₂ | m-Cl | CH₃ | H | |
| 2 | SO₂ | m-Cl | CH₃ | CH₃ | |
| 2 | SO₂ | m-Cl | CH₂CH₃ | H | |
| 2 | SO₂ | m-Cl | CH₂CH₂CH₃ | H | |
| 2 | SO₂ | m-Cl | CH₂CH₂CH₂CH₃ | H | |
| 2 | SO₂ | m-Cl | CH(CH₃)₂ | H | |
| 2 | SO₂ | m-Cl | CH(CH₃)CH₂CH₃ | H | |
| 2 | SO₂ | m-Cl | CH₂CH(CH₃)₂ | H | |
| 2 | SO₂ | o-CH₃ | H | H | |
| 2 | SO₂ | o-CH₃ | CH₃ | H | |
| 2 | SO₂ | o-CH₃ | CH₃ | CH₃ | |
| 2 | SO₂ | o-CH₃ | CH₂CH₃ | H | |
| 2 | SO₂ | o-CH₃ | CH₂CH₂CH₃ | H | |
| 2 | SO₂ | o-CH₃ | CH₂CH₂CH₂CH₃ | H | |
| 2 | SO₂ | o-CH₃ | CH(CH₃)₂ | H | |
| 2 | SO₂ | o-CH₃ | CH(CH₃)CH₂CH₃ | H | |
| 2 | SO₂ | o-CH₃ | CH₂CH(CH₃)₂ | H | |
| 2 | SO₂ | m-CH₃ | H | H | |
| 2 | SO₂ | m-CH₃ | CH₃ | H | |
| 2 | SO₂ | m-CH₃ | CH₃ | CH₃ | |
| 2 | SO₂ | m-CH₃ | CH₂CH₃ | H | |
| 2 | SO₂ | m-CH₃ | CH₂CH₂CH₃ | H | |
| 2 | SO₂ | m-CH₃ | CH₂CH₂CH₂CH₃ | H | |
| 2 | SO₂ | m-CH₃ | CH(CH₃)₂ | H | |
| 2 | SO₂ | m-CH₃ | CH(CH₃)CH₂CH₃ | H | |
| 2 | SO₂ | m-CH₃ | CH₂CH(CH₃)₂ | H | |
| 2 | SO₂ | o-OCH₃ | H | H | |
| 2 | SO₂ | o-OCH₃ | CH₃ | H | |
| 2 | SO₂ | o-OCH₃ | CH₃ | CH₃ | |
| 2 | SO₂ | o-OCH₃ | CH₂CH₃ | H | |
| 2 | SO₂ | o-OCH₃ | CH₂CH₂CH₃ | H | |
| 2 | SO₂ | o-OCH₃ | CH₂CH₂CH₂CH₃ | H | |
| 2 | SO₂ | o-OCH₃ | CH(CH₃)₂ | H | |
| 2 | SO₂ | o-OCH₃ | CH(CH₃)CH₂CH₃ | H | |
| 2 | SO₂ | o-OCH₃ | CH₂CH(CH₃)₂ | H | |
| 2 | SO₂ | m-OCH₃ | H | H | |
| 2 | SO₂ | m-OCH₃ | CH₃ | H | |
| 2 | SO₂ | m-OCH₃ | CH₃ | CH₃ | |

TABLE I-continued

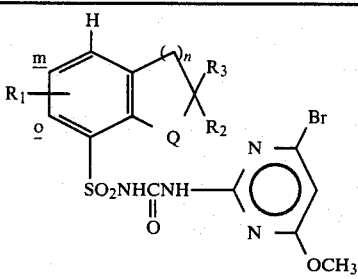

| n | Q | $R_1$ | $R_2$ | $R_3$ | m.p. (°C.) |
|---|---|---|---|---|---|
| 2 | $SO_2$ | m-$OCH_3$ | $CH_2CH_3$ | H | |
| 2 | $SO_2$ | m-$OCH_3$ | $CH_2CH_2CH_3$ | H | |
| 2 | $SO_2$ | m-$OCH_3$ | $CH_2CH_2CH_2CH_3$ | H | |
| 2 | $SO_2$ | m-$OCH_3$ | $CH(CH_3)_2$ | H | |
| 2 | $SO_2$ | m-$OCH_3$ | $CH(CH_3)CH_2CH_3$ | H | |
| 2 | $SO_2$ | m-$OCH_3$ | $CH_2CH(CH_3)_2$ | H | |

TABLE II

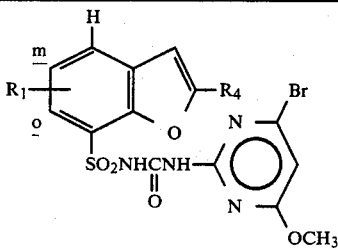

| $R_1$ | $R_4$ |
|---|---|
| H | H |
| H | $CH_3$ |
| o-Cl | H |
| o-Cl | $CH_3$ |
| m-Cl | H |
| m-Cl | $CH_3$ |
| o-$CH_3$ | H |
| o-$CH_3$ | $CH_3$ |
| m-$CH_3$ | H |
| m-$CH_3$ | $CH_3$ |
| o-$OCH_3$ | H |
| o-$OCH_3$ | $CH_3$ |
| m-$OCH_3$ | H |
| m-$OCH_3$ | $CH_3$ |

FORMULATIONS

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few pints to several hundred gallons per acre. High strength compositions are primarily used as intermediates for further formulation. The formulations, broadly, contain about 1% to 99% by weight of active ingredient(s) and at least one of (a) about 0.1% to 20% surfactant(s) and (b) about 5% to 99% solid or liquid diluent(s). More specifically, they will contain these ingredients in the following approximate proportions:

| | Active Ingredient | Percent by Weight Diluent(s) | Surfactant(s) |
|---|---|---|---|
| Wettable Powders | 20-90 | 0-74 | 1-10 |
| Oil Suspensions, | 5-50 | 40-95 | 0-15 |
| Emulsions, Solutions, (including Emulsifiable Concentrates) | | | |
| Aqueous Suspension | 10-50 | 40-84 | 1-20 |
| Dusts | 1-25 | 70-99 | 0-5 |
| Granules and Pellets | 1-95 | 5-99 | 0-15 |
| High Strength Compositions | 90-99 | 0-10 | 0-2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foam, corrosion, microbiological growth, etc. Preferably, ingredients should be approved by the U.S. Environmental Protection Agency for the use intended.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff. and "Perry's Chemical Engineer's Handbook", 4th Ed., McGraw-Hill, New York, 1963, pp. 8-59ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138-40, 162-164, 166, 167 and 169-182;

H. Gysin and E. Knusli, U.S. Pat. No. 2,891,855, June 23, 1959, Col. 3, line 66 through Col. 5, line 17 and Examples 1-4;

G. C. Klingman, "Weed Control as a Science", John Wiley and Sons, Inc., New York, 1961, pp. 81-96;

J. D. Fryer and S. A. Evans, "Weed Control Handbook", 5th Ed., Blackwell Scientific Publications, Oxford, 1968, pp. 101-103;

J. B. Buchanan, U.S. Pat. No. 3,576,834, Apr. 27, 1971, Col. 5, Line 36 through Col. 7, Line 70 and Examples 1-4, 17, 106, 123-140;

R. R. Shaffer, U.S. Pat. No. 3,560,616, Feb. 2, 1971, Col. 3, Line 48 through Col. 7, Line 26 and Examples 3-9, 11-18; and E. Somers, "Formulation", Chapter 6 in Torgeson, "Fungicides", Vol. I, Academic Press, New York, 1967.

In the following examples, all parts are by weight unless otherwise indicated.

EXAMPLE 2

High Strength Concentrate

| | |
|---|---|
| N—[(4-bromo-6-methoxypyrimidin-2-yl)aminocarbonyl]-2,3-dihydrobenzo[b]thiophene-7-sulfonamide, 1,1-dioxide | 99% |
| silica aerogel | 0.5% |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

EXAMPLE 3

Wettable Powder

| | |
|---|---|
| N—[(4-bromo-6-methoxypyrimidin-2-yl)aminocarbonyl]-2,3-dihydrobenzo[b]thiophene-7-sulfonamide, 1,1-dioxide | 90% |
| dioctyl sodium sulfosuccinate | 0.1% |
| synthetic fine silica | 9.9% |

The ingredients are blended and ground in a hammer-mill to produce particles essentially all below 100 microns. The material is sifted through a U.S.S. No. 50 screen and then packaged.

EXAMPLE 4

Wettable Powder

| | |
|---|---|
| N—[(4-bromo-6-methoxypyrimidin-2-yl)aminocarbonyl]-2,3-dihydro-2-methylbenzo[b]thiophene-7-sulfonamide, 1,1-dioxide | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 5

Granule

| | |
|---|---|
| Wettable Powder of Example 4 | 5% |
| attapulgite granules | 95% |
| (U.S.S. 20-40 mesh; 0.84-0.42 mm) | |

A slurry of wettable powder containing ≈25% solids is sprayed on the surface of attapulgite granules in a double-cone blender. The granules are dried and packaged.

EXAMPLE 6

Low Strength Granule

| | |
|---|---|
| N—[(4-bromo-6-methoxypyrimidin-2-yl)aminocarbonyl]-2,3-dihydrobenzo[b]thiophene-7-sulfonamide, 1,1-dioxide | 1% |
| N,N—dimethylformamide | 9% |
| attapulgite granules | 90% |
| (U.S.S. 20-40 sieve) | |

The active ingredient is dissolved in the solvent and the solution is sprayed upon dedusted granules in a double cone blender. After spraying of the solution has been completed, the blender is allowed to run for a short period and then the granules are packaged.

EXAMPLE 7

Granule

| | |
|---|---|
| N—[(4-bromo-6-methoxypyrimidin-2-yl)aminocarbonyl]-2,3-dihydro-2-methylbenzo[b]thiophene-7-sulfonamide, 1,1-dioxide | 80% |
| wetting agent | 1% |
| crude ligninsulfonate salt (containing 5-20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14-100 mesh (1410-149 microns), and packaged for use.

EXAMPLE 8

Extruded Pellet

| | |
|---|---|
| N—[(4-bromo-6-methoxypyrimidin-2-yl)aminocarbonyl]-2,3-dihydrobenzo[b]thiophene-7-sulfonamide, 1,1-dioxide | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 9

Dust

| | |
|---|---|
| N—[(4-bromo-6-methoxypyrimidin-2-yl)aminocarbonyl]-2,3-dihydrobenzo[b]thiophene-7-sulfonamide, 1,1-dioxide | 10% |

| -continued | |
|---|---|
| attapulgite | 10% |
| talc | 80% |

The active ingredient is blended with attapulgite and then passed through a hammer-mill to produce particles substantially all below 200 microns. The ground concentrate is then blended with powdered talc until homogeneous.

EXAMPLE 10

Oil Suspension

| | |
|---|---|
| N—[(4-bromo-6-methoxypyrimidin-2-yl)aminocarbonyl]-2,3-dihydrobenzo[b]thiophene-7-sulfonamide, 1,1-dioxide | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

EXAMPLE 11

Aqueous Suspension

| | |
|---|---|
| N—[(4-bromo-6-methoxypyrimidin-2-yl)aminocarbonyl]-2,3-dihydro-2-methylbenzo[b]thiophene-7-sulfonamide, 1,1-dioxide | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 12

Solution

| | |
|---|---|
| N—[(4-bromo-6-methoxypyrimidin-2-yl)aminocarbonyl]-2,3-dihydrobenzo[b]thiophene-7-sulfonamide, 1,1-dioxide, sodium salt | 5% |
| water | 95% |

The salt is added directly to the water with stirring to produce the solution, which may then be packaged for use.

EXAMPLE 13

Emulsifiable Concentrate

| | |
|---|---|
| N—[(4-bromo-6-methoxypyrimidin-2-yl)aminocarbonyl]-2,3-dihydro-2-methylbenzo[b]thiophene-7-sulfonamide, 1,1-dioxide | 20% |
| chlorobenzene | 74% |
| sorbitan monostearate and polyoxyethylene condensates thereof | 6% |

The ingredients are combined and stirred to produce a solution which can be emulsified in water for application.

Utility

Test results indicate that the compounds of the present invention are highly active preemergent or postemergent herbicides or plant growth regulators. Some of the compounds have particular utility for selective weed control in crops such as soybeans, wheat, barley and cotton. In particular, there is good selective weed control in soybeans.

The rates of application for the compounds of the invention are determined by a number of factors, including their use as plant growth modifiers or as herbicides, the crop species involved, the types of weeds to be controlled, weather and climate, formulations selected, mode of application, amount of foliage present, etc. In general terms, the subject compounds should be applied at levels of around 0.01 to 10 kg/ha, the lower rates being suggested for use on lighter soils and/or those having a low organic matter content, for plant growth modifiers or for situations where only short-term persistence is required.

The compounds of the invention may be used in combination with any other commercial herbicide; examples of which are those of the triazine, triazole, uracil, urea, amide, diphenylether, carbamate and bipyridylium types.

The herbicidal properties of the subject compounds were discovered in a number of greenhouse tests. The test procedures and results follow.

TEST A

Seeds of crabgrass (Digitaria spp.), barnyardgrass (*Echinochloa crusgalli*), wild oats (*Avena fatua*), sicklepod (*Cassia obtusifolia*), morningglory (Ipomoea spp.), cocklebur (*Xanthium pensylvanicum*), sorghum, corn, soybean, cotton, sugar beet, rice, wheat, cotton and purple nutsedge (*Cyperus rotundus*) tubers were planted and treated preemergence with the test chemicals dissolved in a non-phytotoxic solvent. At the same time, these crop and weed species were treated with a soil/foliage application. At the time of treatment, the plants ranged in height from 2 to 18 cm. Treated plants and controls were maintained in a greenhouse for sixteen days, after which all species were compared to controls and visually rated for response to treatment. The ratings, summarized in Table A, are based on a numerical scale extending from 0=no injury, to 10=complete kill. The accompanying descriptive symbols have the following meanings:
B=burn;
C=chlorosis/necrosis;
D=defoliation;
E=emergence inhibition;
G=growth retardation;
H=formative effects;
S=albinism;
U=unusual pigmentation;
X=axillary stimulation; and
6Y=abscised buds or flowers.

The ratings for the compounds tested by this procedure are presented in Table A. It will be seen that, at the low rates of application selected for this test, the compounds tested have utility for plant growth modification and also are highly active herbicides.

Compounds

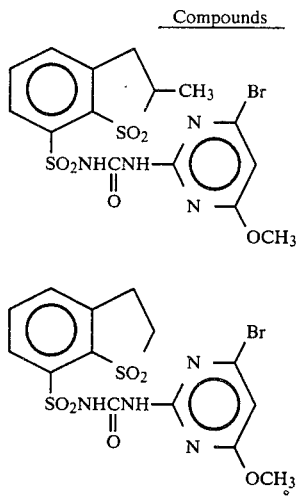

Compound 1

Compound 2

TABLE A

| Rate kg/ha | Cmpd. 1<br>0.05 | Cmpd. 2<br>0.05 |
|---|---|---|
| POSTEMERGENCE | | |
| Morningglory | 3C,6G | 5C,9G |
| Cocklebur | 10C | 6C,9G |
| Sicklepod | 1C,2H | 3C,7G |
| Nutsedge | 3C,8G | 2C,8G |
| Crabgrass | 4C,8G | 6C,9G |
| Barnyardgrass | 10C | 10C |
| Wild Oats | 0 | 0 |
| Wheat | 0 | 2G |
| Corn | 10C | 3C,9G |
| Soybean | 2H,3G | 5G |
| Rice | 5C,9G | 5C,9G |
| Sorghum | 10C | 9C |
| Sugar beet | 9C | 5C,9G |
| Cotton | 4C,9G | 2C,9G |
| PREEMERGENCE | | |
| Morningglory | 9G | 8G |
| Cocklebur | 8G | 9H |
| Sicklepod | 2C,7G | 9G |
| Nutsedge | 10E | 9G |
| Crabgrass | 2G | 2C,8G |
| Barnyardgrass | 4C,8H | 3C,9H |
| Wild Oats | 1C | 1C |
| Wheat | 2G | 2G |
| Corn | 2C,8G | 10E |
| Soybean | 1C,3G | 1H |
| Rice | 10E | 10E |
| Sorghum | 3C,9G | 3C,9H |
| Sugar beet | 10E | 9G |
| Cotton | 9G | 8G |

TEST B

Postemergence

Two round pans (25 cm diameter by 12.5 cm deep) were filled with Woodstown sandy loam soil. One pan was planted with blackgrass (*Alopecurus myosuroides*), sugar beets, nutsedge (*Cyperus rotundus*) tubers, crabgrass (*Digitaria sanquinalis*), sicklepod (*Cassia obtusifolia*), teaweed (*Sida spinosa*), jimsonweed (*Datura stramonium*), velvetleaf (*Abutilon theophrasti*), and giant foxtail (*Setaria faberii*). The other pan was planted with wheat, cotton, rice, corn, soybean, wild oats (*Avena fatua*), cocklebur (*Xantium pensylvanicum*), morningglory (*Ipomoea hederacea*), johnsongrass (*Sorghum halepense*) and barnyardgrass (*Echinochloa crusgralli*). The plants were grown for approximately fourteen days, then sprayed postemergence with the chemicals dissolved in a non-phytotoxic solvent.

Preemergence

Two round pans (25 cm diameter by 12.5 cm deep) were filled with Woodstown sandy loam soil. One pan was planted with blackgrass, sugar beets, nutsedge, crabgrass, sicklepod, teaweed, jimsonweed, velvetleaf, and giant foxtail. The other pan was planted with wheat, cotton, rice, corn, soybeans, wild oats, cocklebur, morningglory, johnsongrass, and barnyardgrass. The two pans were sprayed preemergence with the chemicals dissolved in a non-phytotoxic solvent.

Treated plants and controls were maintained in the greenhouse for 28 days, then all treated plants were compared to controls and visually rated for plant response.

Response ratings are based on a scale of 0 to 10: where 0=no effect, and 10=complete control. The type of response is indicated by letters explained under Test A. A dash (-) response means no test.

Response ratings are contained in Table B.

TABLE B

| | Compound 1 | | | | Compound 2 | | | |
|---|---|---|---|---|---|---|---|---|
| Rate g/ha | 62 | 16 | 4 | 1 | 62 | 16 | 4 | 1 |
| POSTEMERGENCE | | | | | | | | |
| Corn | 10U | 10U | 9G | 7G | 10G | 10G | 9G | 7G |
| Wheat | 0 | 0 | 0 | 0 | 0 | 0 | 0 | 0 |
| Rice | 10C | 9G | 6G | 4G | 10G | 10G | 9G | 7G |
| Soybean | 6G | 4G | 3G | 2G | 3G | 1G | 0 | 0 |
| Cotton | 10C | 8G | 4G | 2G | 9G | 6G | 3G | 0 |
| Sugar beet | 10C | 10G | 9G | 9G | 10G | 7G | 2G | 0 |
| Crabgrass | 10G | 9G | 5G | 2G | 10G | 10G | 8G | 3G |
| Johnsongrass | 10C | 9G | 7G | 3G | 10G | 9G | 9G | 6G |
| Blackgrass | 9C | 8G | 2G | 0 | 10G | 9G | 6G | 2G |
| Barnyardgrass | 10C | 9G | 5G | 2G | 10G | 10G | 7G | 4G |
| Nutsedge | 4G | 2G | 0 | 0 | 0 | 0 | 0 | 0 |
| Giant Foxtail | 9G | 6G | 4G | 0 | 10G | 9G | 7G | 4G |
| Wild Oats | 0 | 0 | 0 | 0 | 0 | 0 | 0 | 0 |
| Cocklebur | 8G | 6G | 3G | 0 | 10G | 6G | 2G | 0 |
| Morningglory | 9G | 8G | 6G | 2G | 10G | 6G | 2G | 0 |
| Teaweed | 10G | 7G | 5G | 2G | 8G | 4G | 0 | 0 |
| Sicklepod | 7G | 4G | 4G | 0 | 4G | 2G | 0 | 0 |
| Jimsonweed | 10G | 5G | 3G | 2G | 10G | 7G | 2G | 0 |
| Velvetleaf | 10C | 6G | 6G | 4G | 10G | 6G | 3G | 0 |
| Rate g/ha | 250 | 62 | 16 | 4 | 250 | 62 | 16 | 4 |
| PREEMERGENCE | | | | | | | | |
| Corn | 10G | 7G | 3G | 0 | 10G | 9G | 4G | 0 |
| Wheat | 0 | 0 | 0 | 0 | 8G | 2G | 0 | 0 |
| Rice | 10G | 10G | 8G | 4G | 10G | 10G | 10G | 8G |
| Soybean | 5G | 2G | 0 | 0 | 6G | 1G | 0 | 0 |
| Cotton | 8G | 3G | 0 | 0 | 9G | 7G | 2G | 0 |
| Sugar beet | 8G | 6G | 2G | 0 | 10G | 9G | 3G | 0 |
| Crabgrass | 10G | 9G | 3G | 0 | 10G | 9G | 8G | 3G |
| Johnsongrass | 10G | 10G | 8G | 3G | 10G | 10G | 9G | 8G |
| Blackgrass | 10G | 10G | 8G | 3G | 10G | 10G | 8G | 7G |
| Barnyardgrass | 10G | 10G | 7G | 2G | 10G | 9G | 9G | 5G |
| Nutsedge | 10G | 9G | 3G | 0 | 10G | 9G | 7G | 3G |
| Giant Foxtail | — | — | — | — | — | — | — | — |
| Wild Oats | 2G | 0 | 0 | 0 | 4G | 0 | 0 | 0 |
| Cocklebur | 7G | 3G | 0 | 0 | 6G | 2G | 0 | 0 |
| Morningglory | 9G | 6G | 3G | 0 | 8G | 3G | 0 | 0 |
| Teaweed | 9G | 8G | 4G | 0 | 10G | 9G | 8G | 2G |
| Sicklepod | 10G | 8G | 4G | 0 | 9G | 7G | 4G | 0 |
| Jimsonweed | 10G | 10G | 8G | 3G | 10G | 9G | 7G | 2G |
| Velvetleaf | 9G | 8G | 3G | 0 | 10G | 8G | 5G | 2G |

TEST C

Three 25-cm diameter plastic pots were filled with a light soil. One pan was planted to short rows of corn, soybeans, and cotton, planting depth 2.5 cm. The other two pots were planted to the following weed species, 8 or 9 species per pot: crabgrass (Digitaria sp.), johnsongrass, (Sorghum halepense), barnyardgrass (Echinochloa crusgalli), nutsedge (Cyperus rotundus), giant foxtail (Setaria faberii), green foxtail (Setaria viridis), cocklebur (Xanthium pensylvanicum), morningglory (Ipomoea hederacea), teaweed (Sida spinosa), sicklepod (Cassia obtusifolia), jimsonweed (Datura stramonium), velvetleaf (Abutilon theophrasti), bindweed (Convolvulus arvensis), coffeeweed (Sesbania exaltata), lambsquarters (Chenopodium album), pigweed (Amaranthus retroflexus), and purslane (Portulaca oleracea). All of the foregoing weed species were planted at a depth of 0.5 to 1.0 cm, except for cocklebur and nutsedge which were planted at a depth of 2.5 cm. The plantings were treated preemergence with the test chemicals dissolved in a non-phytotoxic solvent. At the same time, the same crops and weed species, from plantings made 10 to 21 days previously, were treated with a soil/foliage application. Treated plants and controls were maintained in a greenhouse for 3 to 4 weeks after which all species were compared to controls and visually rated for response to treatment with 0 indicating no injury and 100 indicating that the plants were dead. The data are summarized in Table C.

pan was planted with seeds of wheat (Triticum aestivum), barley (Hordeum vulgare), wild oats (Avena fatua), cheatgrass (Bromus secalinus), blackgrass (Alopecurus myosuroides), annual bluegrass (Poa annua), green foxtail (Setaria viridis), Italian ryegrass (Lolium multiflorum) and rapeseed (Brassica napus). The other pan was planted with seeds of Russian thistle (Salsola kali), cleavers (Galium aparine), speedwell (Veronica persica), kochia (Kochia scoparia), shepherdspurse (Capsella bursa-pastoris), Matricaria inodora, black nightshade (Solanum nigrum), wild buckwheat (Polygonum convolvulus) and sugar beets (Beta vulgaris). The above two pans were treated preemergence. At the same time two pans in which the above plant species were already growing were treated postemergence. Plant height at the time of treatment ranged from 1–20 cm depending on plant species.

The compounds applied were diluted with a non-phytotoxic solvent and sprayed over-the-top of the pans. An untreated control and a solvent alone control were included for comparison. All treatments were maintained in the greenhouse for 19–22 days at which time the treatments were compared to the controls and the effects visually rated utilizing the same rating sys-

TABLE C

| Rate gm/ha | Compound 1 | | | | | | | Compound 2 | | | | | | |
|---|---|---|---|---|---|---|---|---|---|---|---|---|---|---|
| | 250 | 125 | 62 | 31 | 16 | 8 | 4 | 250 | 125 | 62 | 31 | 16 | 8 | 4 |
| POSTEMERGENCE | | | | | | | | | | | | | | |
| Corn | 100 | 100 | 100 | 100 | 90 | 85 | 80 | 100 | 100 | 100 | 100 | 90 | 85 | 75 |
| Cotton | — | — | — | — | — | — | — | — | — | — | — | — | — | — |
| Soybean | 55 | 40 | 35 | 30 | 25 | 20 | 20 | 45 | 40 | 30 | 25 | 20 | 15 | 0 |
| Crabgrass | 100 | 100 | 95 | 85 | 75 | 65 | 40 | 100 | 95 | 95 | 85 | 75 | 50 | 35 |
| Johnsongrass | 100 | 100 | 100 | 100 | 100 | 100 | 80 | 100 | 100 | 100 | 100 | 100 | 95 | 85 |
| Barnyardgrass | 100 | 100 | 100 | 95 | 80 | 75 | 50 | 100 | 100 | 100 | 90 | 85 | 80 | 65 |
| Nutsedge | 100 | 95 | 80 | 75 | 55 | 35 | 30 | 95 | 85 | 80 | 75 | 50 | 20 | 0 |
| Giant foxtail | 100 | 100 | 100 | 95 | 85 | 80 | 70 | 100 | 100 | 95 | 90 | 85 | 80 | 70 |
| Green foxtail | 100 | 100 | 100 | 95 | 85 | 85 | 70 | 100 | 100 | 100 | 90 | 90 | 85 | 70 |
| Cocklebur | — | 100 | 100 | 85 | 65 | 40 | 100 | 100 | 90 | 85 | 70 | 65 | 40 | 20 |
| Morningglory | — | 95 | 90 | 80 | 75 | 55 | 35 | 95 | 85 | 80 | 70 | 70 | 50 | 30 |
| Teaweed | — | 90 | 85 | 80 | 80 | 60 | 40 | 100 | 90 | 90 | 65 | 60 | 50 | 35 |
| Sicklepod | — | 90 | 85 | 80 | 65 | 50 | 40 | 100 | 95 | 85 | 70 | 55 | 25 | 15 |
| Jimsonweed | — | 85 | 80 | 85 | 75 | 50 | 40 | 100 | 90 | 80 | 50 | 40 | 20 | 15 |
| Velvetleaf | 95 | 90 | 85 | 80 | 65 | 40 | 30 | 95 | 85 | 75 | 75 | 55 | 25 | 20 |
| Bindweed | 85 | 60 | 40 | 35 | 25 | 15 | 0 | 70 | 60 | 60 | 45 | 40 | 25 | 15 |
| Coffeeweed | 100 | 100 | 100 | 85 | 80 | 65 | 45 | 100 | 100 | 90 | 65 | 60 | 35 | 25 |
| Lambsquarter | 100 | 95 | 90 | 90 | 70 | 60 | 35 | 100 | 100 | 95 | 90 | 80 | 40 | 15 |
| Pigweed | 100 | 100 | 100 | 100 | 85 | 75 | 40 | 100 | 100 | 100 | 100 | 95 | 80 | 45 |
| Purslane | 100 | 100 | 95 | 85 | 75 | 65 | 50 | 100 | 100 | 100 | 85 | 85 | 40 | 35 |
| PREEMERGENCE | | | | | | | | | | | | | | |
| Corn | 100 | 100 | 95 | 85 | 75 | 45 | 20 | 100 | 100 | 95 | 80 | 60 | 20 | 0 |
| Cotton | 100 | 100 | 85 | 75 | 35 | 15 | 0 | 100 | 90 | 70 | 25 | 15 | 0 | 0 |
| Soybean | 75 | 40 | 25 | 0 | 0 | 0 | 0 | 50 | 35 | 20 | 0 | 0 | 0 | 0 |
| Crabgrass | 100 | 100 | 100 | 100 | 85 | 60 | 20 | 100 | 100 | 100 | 100 | 85 | 75 | 55 |
| Johnsongrass | 100 | 100 | 100 | 100 | 100 | 95 | 75 | 100 | 100 | 100 | 100 | 100 | 90 | 85 |
| Barnyardgrass | 100 | 100 | 100 | 100 | 95 | 85 | 35 | 100 | 100 | 100 | 100 | 90 | 85 | 55 |
| Nutsedge | 100 | 100 | 100 | 100 | 95 | 85 | 45 | 100 | 100 | 100 | 95 | 75 | 45 | 25 |
| Giant foxtail | 100 | 100 | 100 | 95 | 90 | 30 | 0 | 100 | 100 | 100 | 90 | 85 | 80 | 20 |
| Green foxtail | 100 | 100 | 95 | 95 | 80 | 15 | 0 | 100 | 100 | 100 | 90 | 90 | 55 | 15 |
| Cocklebur | 100 | 100 | 85 | 55 | 35 | 25 | 0 | — | — | — | — | — | — | — |
| Morningglory | 100 | 100 | 95 | 90 | 85 | 35 | 0 | 100 | 100 | 100 | 85 | 60 | 20 | 0 |
| Teaweed | 100 | 100 | 100 | 85 | 75 | 45 | 15 | 100 | 100 | 95 | 85 | 55 | 25 | 15 |
| Sicklepod | 100 | 100 | 95 | 85 | 65 | 45 | 15 | 100 | 90 | 90 | 75 | 40 | 20 | 15 |
| Jimsonweed | 100 | 100 | 100 | 95 | 90 | 60 | 20 | 100 | 100 | 100 | 100 | 100 | 90 | 75 |
| Velvetleaf | 100 | 100 | 95 | 95 | 80 | 65 | 15 | 100 | 95 | 90 | 80 | 50 | 25 | 15 |
| Bindweed | 100 | 100 | 90 | 85 | 75 | 55 | 25 | 100 | 95 | 90 | 85 | 80 | 60 | 45 |
| Coffeeweed | 100 | 100 | 85 | 80 | 60 | 35 | 15 | 100 | 90 | 90 | 80 | 45 | 30 | 20 |
| Lambsquarter | 100 | 100 | 100 | 100 | 90 | 75 | 50 | 100 | 100 | 100 | 100 | 90 | 80 | 75 |
| Pigweed | 100 | 100 | 100 | 100 | 90 | 75 | 50 | 100 | 100 | 100 | 100 | 90 | 80 | 75 |
| Purslane | 100 | 100 | 100 | 100 | 100 | 80 | 50 | 100 | 100 | 100 | 100 | 100 | 85 | 80 |

TEST D

Two plastic pans lined with polyethylene liners were filled with prepared Woodstown sandy loam soil. One pan was planted with seeds of wheat (Triticum aestem as described for Test A. The recorded data are presented in Table D.

TABLE D

| Rate kg/ha | Compound 1 | | | | | | | | Compound 2 | | | | | | | |
|---|---|---|---|---|---|---|---|---|---|---|---|---|---|---|---|---|
| | .125 | .06 | .03 | .015 | .008 | .004 | .002 | .0001 | .125 | .06 | .03 | .015 | .008 | .004 | .002 | .0001 |
| POSTEMERGENCE | | | | | | | | | | | | | | | | |
| wheat | 2G | 0 | 0 | 0 | 0 | 0 | 0 | 0 | 0 | 0 | 0 | 0 | 0 | 0 | 0 | 0 |
| barley | 8G | 5G | 4G | 3G | 2G | 0 | 0 | 0 | 6G | 5G | 4G | 4G | 5G | 2G | 2G | 0 |
| wild oats | 0 | 0 | 0 | 0 | 0 | 0 | 0 | 0 | 0 | 0 | 0 | 0 | 0 | 0 | 0 | 0 |
| cheatgrass | 6G | 5G | 3G | 0 | 0 | 0 | 0 | 0 | 6G | 4G | 4G | 2G | 0 | 0 | 0 | 0 |
| blackgrass | 10C | 9G | 7G | 5G | 3G | 0 | 0 | — | 9G | 9G | 8G | 5G | 3G | 0 | 0 | — |
| annual bluegrass | 10C | 9G | 9G | 4G | 4G | 0 | 0 | — | 10C | 9G | 8G | 5G | 2G | 2G | 0 | — |
| green foxtail | 10C | 10C | 10C | 10C | 8G | 6G | 4G | — | 10C | 10C | 10C | 10C | 8G | 7G | 5G | — |
| Italian ryegrass | 10C | 8G | 8G | 5G | 3G | 2G | 2G | — | 9G | 6G | 5G | 3G | 2G | 0 | 0 | — |
| rapeseed | 10C | 10C | 10C | 10C | 10C | 9G | 7G | — | 10C | 10C | 10C | 10C | 9G | 8G | 5G | — |
| *Matricaria inodora* | — | — | — | — | — | — | — | — | — | — | — | — | — | — | — | — |
| *Galium aparine* | — | — | — | — | — | — | — | — | — | — | — | — | — | — | — | — |
| Russian thistle | — | — | — | — | — | — | — | — | — | — | — | — | — | — | — | — |
| shepherdspurse | — | — | — | — | — | — | — | — | — | — | — | — | — | — | — | — |
| kochia | — | — | — | — | — | — | — | — | — | — | — | — | — | — | — | — |
| black nightshade | — | — | — | — | — | — | — | — | — | — | — | — | — | — | — | — |
| speedwell | 10C | 10C | 10C | 3G | 0 | 0 | 0 | 0 | 7G | 0 | 0 | 0 | 0 | 0 | 0 | 0 |
| wild buckwheat | 10C | 5G | 2G | 0 | — | 2G | 2G | 0 | 7G | 2G | 2G | — | 0 | 0 | 0 | 0 |
| sugar beets | 10C | 9G | 9G | 4G | 5G | 3G | 3G | 3G | 10C | 10C | 10C | 4G | 3G | 3G | 0 | 0 |
| PREEMERGENCE | | | | | | | | | | | | | | | | |
| wheat | 0 | 0 | 0 | 0 | 0 | 0 | 0 | 0 | 0 | 0 | 0 | 0 | 0 | 0 | 0 | 0 |
| barley | 6G | 0 | 2G | 0 | 0 | 0 | 0 | 0 | 8G | 7G | 7G | 7G | 3G | 3G | 0 | 0 |
| wild oats | 0 | 0 | 0 | 0 | 0 | 0 | 0 | 0 | 0 | 0 | 0 | 0 | 0 | 0 | 0 | 0 |
| cheatgrass | 5G | 2G | 0 | 0 | 0 | 0 | 0 | 0 | 7G | 3G | 0 | 0 | 0 | 0 | 0 | 0 |
| blackgrass | 8G | 8G | 8G | 8G | 7G | 3G | 2G | 0 | 9G | 8G | 8G | 7G | 6G | 4G | 2G | 1G |
| annual bluegrass | 9G | 9G | 9G | 8G | 8G | 7G | 5G | 3G | 9G | 9G | 9G | 8G | 5G | 5G | 3G | 2G |
| green foxtail | 9G | 8G | 5G | 2G | 0 | 0 | 0 | 0 | 9G | 7G | 7G | 6G | 4G | 2G | 0 | 0 |
| Italian ryegrass | 8G | 8G | 7G | 4G | 4G | 3G | 3G | 0 | 8G | 7G | 6G | 5G | 4G | 2G | 2G | 2G |
| rapeseed | 9G | 9G | 9G | 8G | 7G | 4G | 4G | 2G | 9G | 9G | 9G | 7G | 5G | 2G | 2G | 2G |
| *Matricaria inodora* | 9G | 9G | 8G | 8G | 8G | 6G | 6G | 5G | 8G | 7G | 7G | 7G | 6G | 5G | 4G | 3G |
| *Galium aparine* | 10C | 9G | 9G | 5G | 5G | 4G | 4G | 0 | 9G | 8G | 9G | 6G | 5G | 0 | 0 | 0 |
| Russian thistle | 8G | 8G | 3G | 2G | 2G | 2G | 0 | 0 | 6G | 6G | 3G | 0 | 0 | 0 | 0 | 0 |
| shepherdspurse | 10C | 10C | 9G | 9G | 9G | 7G | 6G | 0 | 10C | 10C | 9G | 9G | 8G | 6G | 5G | 3G |
| kochia | 10C | 10C | 10C | 10C | 8G | 8G | 4G | 4G | 10C | 10C | 10C | 9G | 7G | 6G | 6G | 3G |
| black nightshade | 9G | 9G | 9G | 8G | 8G | 6G | 3G | 0 | 9G | 9G | 9G | 8G | 8G | 8G | 6G | 4G |
| speedwell | 10C | 10C | 10C | 10C | 9G | 7G | 5G | 0 | 9G | 6G | 3G | 0 | 0 | 0 | 0 | 0 |
| wild buckwheat | 8G | 8G | 7G | 2G | 0 | 0 | 0 | 0 | 8G | 5G | — | 0 | 0 | 0 | 0 | 0 |
| sugar beets | 10C | 10C | 10C | 10C | 8G | 8G | 6G | 6G | 9G | 9G | 9G | 9G | 7G | 8G | 5G | 5G |

What is claimed is:

1. The compound N-[(4-bromo-6-methoxypyrimidin-2-yl)aminocarbonyl]-2,3-dihydrobenzo[b]thiophene-7-sulfonamide, 1,1-dioxide.

2. The compound N-[(4-bromo-6-methoxypyrimidin-2-yl)aminocarbonyl]-2,3-dihydro-2-methylbenzo[b]thiophene-7-sulfonamide, 1,1-dioxide.

3. A composition suitable for controlling the growth of undesired vegetation which comprises an effective amount of the compound of claim 1 and at least one of the following: surfactant, solid or liquid diluent.

4. A composition suitable for controlling the growth of undesired vegetation which comprises an effective amount of the compound of claim 2 and at least one of the following: surfactant, solid or liquid diluent.

5. A method for controlling the growth of undesired vegetation which comprises applying to the locus to be protected an effective amount of the compound of claim 1.

6. A method for controlling the growth of undesired vegetation which comprises applying to the locus to be protected an effective amount of the compound of claim 2.

* * * * *